United States Patent [19]

Törmälä et al.

[11] Patent Number: 4,655,203

[45] Date of Patent: Apr. 7, 1987

[54] BONE FRACTURE SURGICAL DEVICE

[75] Inventors: Pertti Törmälä, Tampere; Pentti Rokkanen, Helsinki; Jyrki Kilpikari, Tampere; Hannu Pätiälä, Helsinki; Seppo Vainionpää, Helsinki; Kimmo Vihtonen, Helsinki; Matti Mero, Helsinki, all of Finland

[73] Assignee: Materials Consultants Oy, Tampere, Finland

[21] Appl. No.: 649,648

[22] Filed: Sep. 12, 1984

[30] Foreign Application Priority Data

Sep. 20, 1983 [FI] Finland ................................. 833351

[51] Int. Cl.⁴ ............................................. A61F 5/04
[52] U.S. Cl. ................................. 128/92 YP; 128/89 A; 128/92 C; 623/16; 433/173
[58] Field of Search ................. 128/92 R, 92 A, 92 B, 128/92 C, 92 D; 32/10 A

[56] References Cited

U.S. PATENT DOCUMENTS

| 2,502,902 | 4/1950 | Tofflemire . | |
|---|---|---|---|
| 2,825,329 | 3/1958 | Caesar | 128/92 R |
| 3,710,789 | 1/1973 | Ersek | 128/92 G |
| 3,955,567 | 5/1976 | Richmond et al. | 128/92 D |

FOREIGN PATENT DOCUMENTS

| 2340880 | 4/1975 | Fed. Rep. of Germany . |
| 2904304 | 8/1979 | Fed. Rep. of Germany . |
| 3100431 | 4/1982 | Fed. Rep. of Germany . |
| 960010 | 4/1950 | France . |
| 618866 | 8/1980 | Switzerland . |
| 1517161 | 7/1978 | United Kingdom . |

Primary Examiner—Robert P. Swiatek
Assistant Examiner—Wenceslao J. Contreras
Attorney, Agent, or Firm—Pollock, Vande Sande & Priddy

[57] ABSTRACT

Surgical device for immobilization of bone fracture, which device comprises at least one, essentially stiff osteosynthesis plate (7) which is located perpendicularly over or through the fracture (6). Additionally the osteosynthesis device comprises at least one firm fixing element (8, 8') which is fastened to bone (5) and/or tightened to its place to go beyond or to perforate the fracture (6) and/or to go beyond the osteosynthesis plate (7) in such a way that the osteosynthesis plate (7), the tightened fixing element (8, 8', 8'') and the region of immobilized bone (5) where the fracture (6) exists form an assembly whose stiffness is high enough to confirm the healing of the fracture (6) and that as a consequence of resorption of osteosynthesis plate (7) during the healing of the fracture (6) the stiffness and mechanical strength of the surgical device decrease in such a way that the need to remove the surgical device or part of it at a separate subsequent operation is excluded.

15 Claims, 20 Drawing Figures

BONE FRACTURE SURGICAL DEVICE

TECHNICAL FIELD

This invention relates to surgical devices which are defined more exactly in claim 1.

BACKGROUND OF THE INVENTION

In traumatology has been accepted generally the method to use surgical devices (osteosynthesis devices), where the parts of broken bone are held together (immobilized) by means of plate-like, perforated osteosynthesis plates, which are fixed to bone by screws, to immobilize the fractured bone during the healing period.

The demands of such surgical devices are very high because they must have sufficient mechanical properties, be compatible with the tissues and they must permit undisturbed osseous union. Usually such surgical devices have been manufactured of austenitic steel, titan or of other metals or metal alloys, which fulfill the demands of tissue environment. Generally such conventional biostable surgical devices are removed at a separate subsequent operation, when the healing of the fracture has proceeded by means of the growth of the bone tissue far enough.

The use of metallic surgical elements causes, however, many kinds of problems. Many metals and metal alloys corrode in tissues causing inflammation and infections, which are problematic and are eliminated only after removing the surgical device. The corrosion is often found in contact points of plates and screws.

Because of the large difference in stiffness between bone (Youngs modulus $E = 6-20$ GPa) and metals ($E = 100-200$ GPa), rigid metallic fixation prevents the rapid proliferation of primary callus and deprives the bone of the normal stress-pattern. The long-term result of stress-protection is a mechanically inferior bone structure in the region of the plate because of osteoporosis and atrophy. Refracture is therefore a possibility after the removal of the plate.

The possibilities to use other than metallic materials as surgical devices have been studied extensively during last years. On the basis of these studies polymers and polymer composites seem to be in this respect promising materials.

Polymers and composites which are useful as surgical implant-materials can be classified to biostable and totally or partially resorbable. Accordingly surgical devices can be classified to biostable, resorbable and to at least partially resorbable.

The reaction, which biostable polymeric surgical devices cause to tissue, is minimal and the implant retains its form and properties practically unchanged even during long periods of time (typically years). Such a surgical device has been defined e.g. in a Swiss Pat. No. 618 866.

Totally resorbable and at least partially resorbable polymeric or composite surgical devices retain their tissue-supporting properties certain periods of time (typically weeks of months) and they are gradually degraded biologically into tissue compatible components which are absorbed by living tissues and replaced by healing tissues. In the case of partially resorbable devices a non-supporting encapsulated remnant of device can remain in tissue.

When one uses biostable polymeric surgical devices, whose modulus is the same order of magnitude as the modulus of bone, one can diminish the disadvantages of osteoporosis and metallic corrosion remarkably. However, these devices in many cases must be removed at a separate operation. When one manufactures surgical devices of totally or at least partially resorbable polymers or composites it is possible to avoid the removal operation. Therefore the at least partially resorbable surgical devices are the best one alternative because of the following reasons:

(B 1) At the early stage of healing of fracture the at least partially resorbable device preserves the required bone immobilization. At the later stage the device decomposes gradually and the stresses are transferred gradually to the healing bone. This prevents osteoporosis.

(2) The mechanical properties of the surgical devices which are manufactured of organic material or composite can be regulated nearer to the corresponding properties of bone than the properties of metallic implants.

(3) Totally or at least partially resorbable surgical devices do not need the removal operation which means substantial economical and human advantages.

The most studied in surgery applicable resorbable polymers are polyglycolides, polylactides and their copolymers. Their manufacturing and applications as sutures etc. are disclosed in several patents e.g. in U.S. Pat. No. 2,668,162, U.S. Pat. No. 2,676,945, U.S. Pat. No. 3,297,033, U.S. Pat. No. 3,463,158, U.S. Pat. No. 3,636,956 and Can. Pat. No. 808 731. U.S. Pat. No. 3,297,033 discloses the principle to use polyglycolide fibers in conjunction with other structures as prosthetic devices. This principle is applied in French Pat. Appl. No. 78 29878 which discloses the resorbable surgical device of polylactide which in reinforced with resorbable polyglycolide fibers. An application of this invention discloses a perforated surgical device which is screwed to bone with stainless steel screws (P. Christel et al., Biomaterials 1980, p. 271).

U.S. Pat. No. 3,463,158 discloses the resorbable sheet of polyglycolic acid which is fixed to the bisected ends of femurs of the hind legs of rabbits by means of polyglycolic nails which are driven through the holes in the polyglycolic plate and bone.

FIG. 1 shows schematically the conventional surgical osteosynthesis device fixed to bone. According to FIG. 1 the bone 1, which includes the fracture 2, is immobilized by means of the osteosynthesis plate 3 which goes beyond the fracture 2 and which is fixed to the bone by means of nails or screws 4. The number of screws is typically between 6-8.

Also other publications which handle applications of at least partially resorbable materials as surgical devices disclose fixation techniques which apply perforated plates.

The fixation of perforated plates by screws or nails is suitable for metals because the compressive stresses caused by screwing or nailing to the plate as a rule do not exceed the yield strength of the metal. So the metallic materials behave in these conditions elastically.

Surgical devices which are manufactured of polymers or polymer composites are viscoelastic of their mechanical behavior. Therefore they do not have a clear region of elastic behaviour. Therefore the compressive stresses caused by nailing or screwing around the fixing hole cause in these devices continuous deformation (creep), which leads to the enlargening of the hole which causes the loosening of fixation and/or the formation of fractures around the hole. Additionally polymeric materials are notch sensitive and therefore the fixation holes act as harmful points of stress concentrations which also promotes the formation of fractures around the holes (P. Christel et al., Biomaterials, 1980, p. 271).

Additionally the screw fixation of plates causes to the screw-bone boundary strong local torsional stresses, which means that this boundary is the weakest point in such constructions.

DISCLOSURE OF THE INVENTION

This invention relates to a synthetic, at least partially resorbable surgical device, by means of which it is possible to eliminate the above discussed problems which especially originate from the conventional screw-fixation technique. The invention relates also to the construction which is strong enough to fulfill its purpose but which does not need the separate surgical removal operation.

To the surgical device of the invention is mainly characteristic that it comprises a combination of:

at least one, at least directly after surgical installation operation essentially stiff, at least partially resorbable osteosynthesis plate or beam which goes beyond or perforates the fracture and of at least one at least during the surgical installation flexible fixing element which is fastened to bone and/or tightened to its place to go beyond or to perforate the fracture and/or to go beyond the osteosynthesis plate in such a way that the osteosynthesis plate, the tightened fixing element and the region of immobilized bone where the fracture exists form the whole whose stiffness is high enough to confirm the healing of the fracture and that as a consequence of resorption of osteosynthesis plate during the healing of the fracture the stiffness and mechanical strength of the surgical device decrease strongly which excludes the need to remove the surgical device or part of it at a separate subsequent operation.

By using the surgical device of this invention it is possible to utilize, both during the surgical operation and during the healing period, the very mechanical properties of the basic components (in the beginning stiff plate and flexible fixing element) and the properties of plate or plate and fixing element which change as a consequence of resorption.

The fixing element can be flexible or stiff in such a way that its stiffness is accomplished during the final stage of the surgical installation operation.

A typical flexible fixing element is a thread, filament bundle, strand, braid, band or corresponding structure which is constructed of resorbable and/or biostable fibers. A typical stiff fixing element is a thread, filament bundle, strand, braid, band or corresponding structure which is constructed of resorbable and/or biostable fibers which are coated or impregnated with a polymer, reactive oligomer or monomer.

The following Tables characterize qualitatively some mechanical, from the point of view of immobilization operation, important properties of the basic components of the invented device. This examination characterizes the situation directly after the surgical installation of device to immobilize the bone fracture.

TABLE 1

Properties of at least partially resorbable osteosynthesis plate and flexible fixing element directly after surgical installation

| Property | Osteosynthesis plate | Fixing element |
| --- | --- | --- |
| Bending strength | Excellent | Faint or nondefinable |
| Torsional strength | Excellent | Faint or nondefinable |
| Tensile strength | Good | Excellent |
| Youngs modulus | Good | Excellent |
| Bending- and torsional modulus | Good | Faint or nondefinable |
| Stiffening effect upon fracture | Excellent | Moderate |
| Fastening to bone | Faint or Moderate | Excellent |

TABLE 2

Properties of at least partially resorbable osteosynthesis plate and stiff fixing element directly after surgical installation

| Property | Osteosynthesis plate | Fixing element |
| --- | --- | --- |
| Tensile strength | Good | Excellent |
| Stiffening effect upon fracture | Excellent | Moderate |
| Fastening to bone | Faint or Moderate | Excellent |

Scale: Excellent, good, moderate, faint.

According to Tables 1 and 2 the osteosynthesis plate and the fixing element of the invention both have good and poor properties separately. When these components are combined according to the invention it is possible to eliminate the poor properties of components (such as the faint fastening of osteosynthesis plate to bone and the insufficient stiffening effect of fixing element). Therefore the fracture can be immobilized effectively against deformations which different external forces try to induce to the fracture surfaces.

Because in the surgical device of invention the osteosynthesis plate or both the osteosynthesis plate and the fixing element are manufactured at least partially of resorbable material, the decreasing of the stiffness and mechanical strength of the device begins directly after the installation operation has been accomplished. When this decrease of mechanical strength and stiffness occurs slowly enough it is an advantageous phenomenon because, on the other hand, the stiffness and strength of healing fracture increase as a function of time. When the absorption of surgical device has proceeded far enough its strength and stiffness decrease to such a low level (most profitably to zero) that the surgical device has not any more importance as a stiffener and supporter of the healing or healed bone. Then the surgical device do not cause osteoporosis or other mechanical disturbances, either. If the partially resorbable device does not cause even during long periods of time tissue irritation or other harmful reactions, the removal operation is not necessary. An especially advantageous embodiment of invention is the device which is manufactured of totally resorbable materials as in the case of EXAMPLE 1. In such cases both the osteosynthesis plate and the fixing element are absorbed completely during the healing process or after it and the need of removing operation is naturally eliminated.

The surgical device of the invention has several advantages in comparison to conventional biostable (polymeric and metallic) and resorbable devices. Because the device of invention does not contain holes which are necessary for nail or screw fixation, the stresses are distributed in a decisive way more evenly over the whole system than in conventional devices, where stress concentrations are formed around holes and torsional stresses are developed between screws and bone. As a consequence the invention makes possible to apply in surgical devices such materials as resorbable polymers and composites which are less stiff and which resemble better as far as their mechanical properties are concerned the same of bone tissue than conventional metallic materials. The devices of the invention also aliminate the weak screw-bone interfaces.

The mechanical properties of devices of the invention can be regulated extensively (also as a function of time) when their components are manufactured of (a) resorbable materials, (b) resorbable and biostable materials, (c) their composite materials and (d) by combining in different ways the basic components (stiff plates and firm, flexible fixing elements). So it is possible to select optimal osteosynthesis devices taking into account the process of healing and the procedures of operation in each fracture case.

BRIEF DESCRIPTION OF THE DRAWINGS

In the following specification the invention is described more closely with reference to the enclosed drawings, in which.

DESCRIPTION OF BEST MODE AND OTHER EMBODIMENTS OF THE INVENTION

Figure 1:
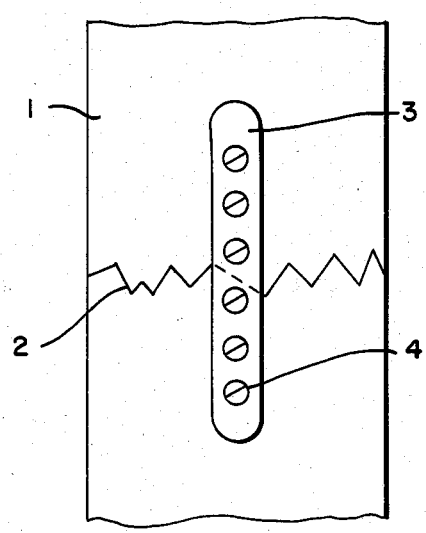
FIG. 1 shows schematically the conventional surgical osteosynthesis device fixed to a bone.

The invention and its function is illustrated in FIG. 2. When the surgical device of the invention is installed in its place it comprises (a) at least one, at least directly after surgical installation operation, essentially stiff, at least partially resorbable osteosynthesis plate 7, which goes beyond or perforates the fracture 6 of bone 5 and (b) at least one, at least during installation, flexible firm fixing element 8. The bone which will be immobilized can be equipped with at least one groove 9, 9' and 9" (the dash line in FIGS. 2a–e, h and i) and/or channel 11 (the dash line in FIG. 2f) into which the osteosynthesis plate or part of it will be pressed to intensify the immobilization effect. The depth of groove 9 can be changed, so that e.g. in long bones it can reach the marrow cavity. One can also use on bone-osteosynthesis plate boundary some suitable adhesion promotor such as cyanoacrylate adhesive.

Figure 2A:
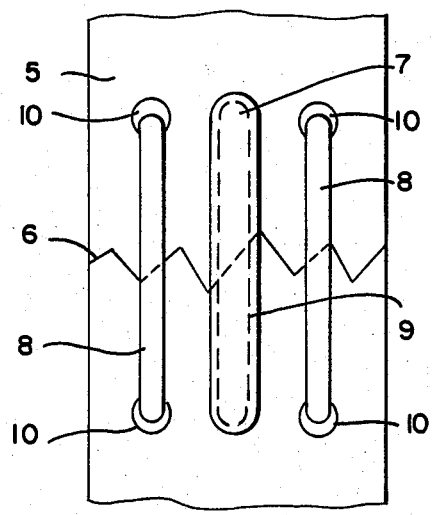
FIGS. 2a–2i show application examples of the device of invention looked from above of the fracture.

If to the bone are directed strong tensile stresses, but only weak bending or torsional stresses, one can use the construction of FIG. 2a, where at least one osteosynthesis plate 7 is pressed into the groove 9 which is done into bone. The staying of plate at its place can still be confirmed by means of a suitable adhesion promoter such as cuanoacrylate adhesive. In the case of FIG. 2a the fixing elements 8 go beyond the fracture and they have been installed in their place by threading the fixing element cord through holes 10 which have been drilled into bone on the both sides of the fracture and by tightening and joining (s.g. by knotting) the cords to ring-shaped structures. When one uses firm fixing elements which have been manufactured e.g. of resorbable fibers, the opening effect of tensile stresses upon fracture is effectively prevented at the same time when the osteosynthesis plate prevents deformations in transverse direction. The immobilization effect of this surgical device is strongest directly after the installation operation when the strength of the healing fracture is at its weakest. The immobilization effect of the device decreases favourably as a function of time as a consequence of resorption of the osteosynthesis plate (and possibly of the fixing element, too) at the same time when the fracture gains strength when the healing advances. If it is question about stiff fixing element, one can use technique where the holes 10 do not necessarily go through the bone but they form notches into which the stiff fixing elements are pressed.

Figure 2B:
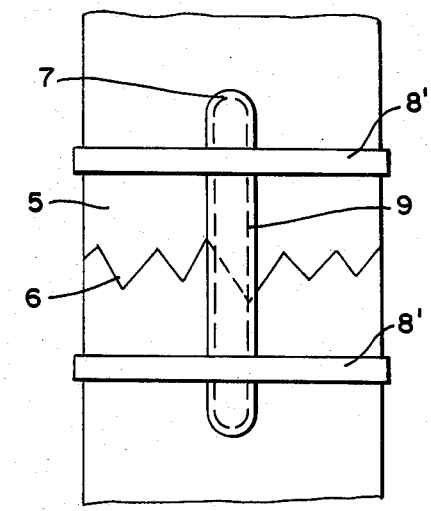
Figure 2C:
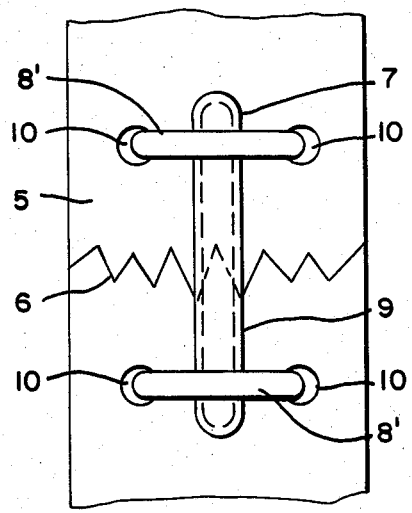

If strong bending stresses to the fracture are directed, but only weak tensile stresses, the constructions of FIGS. 2b and 2c can be applied. In this case at least one osteosynthesis plate 7 is pressed mechanically by means of at least one fixing element 8' against the bone which one wants to immobilize. Stiff and flexible fixing elements can be ring-shaped and they can go around the entire bone as in FIG. 2b. The flexible fixing elements can be threaded through holes which are drilled through the bone as in FIG. 2c.

The stiffening fixing elements can also be pressed from above into holes 10 in the case of FIG. 2c.

Due to the compression which the fixing elements cause to the osteosynthesis plate, the osteosynthesis plate 7, the fixing elements 8' and the region of fracture 6 of bone 5 form an assembly which bears effectively bending stresses. The strength of the construction can be further improved by locating the osteosynthesis plate 7 at least partially into the groove 9 which is done into the bone and/or by using between the osteosynthesis plate and bone a suitable adhesion promoter such as cyanoacrylate adhesive. The strength and stiffness of the surgical device decrease favourably as a function of time during healing when the resorption of osteosynthesis plate (and possibly of the fixing element, too) proceeds.

Figure 2D:
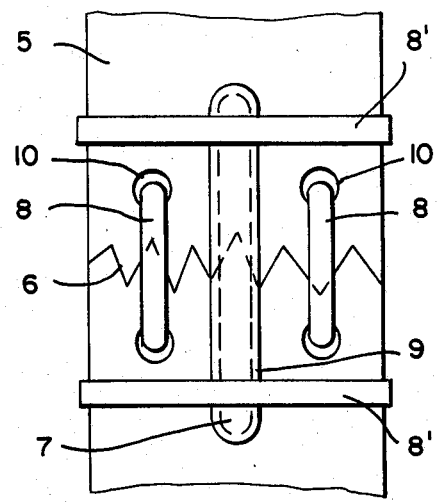

If very strong stresses of a different kind are directed to the fracture (as e.g. in the case of long bones), the construction of FIG. 2d can be used. Also in this case the osteosynthesis plate 7 is pressed mechanically against the bone 5 by means of fixing elements 8' which go around the bone. The strength of the construction can be improved if the osteosynthesis plate 7 is pressed at least partially into the groove 9 which is done into the bone 5. Further in the construction of FIG. 2d are used fixing elements 8, which go beyond the fracture 6, to press the fracture surfaces of bone 5 directly against each other. The fixing elements 8 can be mounted to their place e.g. by the ways which are presented in the explanation of FIG. 2a.

Figure 2E:
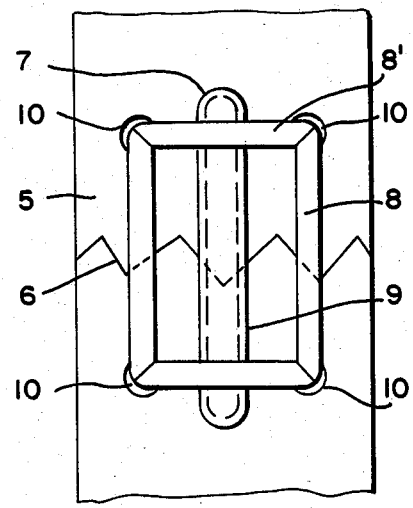

The fixing elements 8 and 8' can be constructed also of a continuous resorbable and/or biostable cord or band, which is threaded through holes or pressed into holes which are drilled into the bone. Such a construction is shown in FIG. 2e where the continuous fixing element 8 and 8' causes the compression directly both to the oteosynthesis plate 7 and to the fracture surfaces of bone 5. The level of compression diminishes and therefore also the stiffness of the device decreases favourably when the resorption of the osteosynthesis plate (and possibly of the fixing element, too) proceeds as a function of time during the healing of fracture.

Figure 2F:
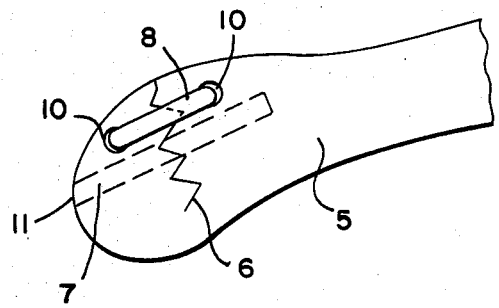
Figure 2G:
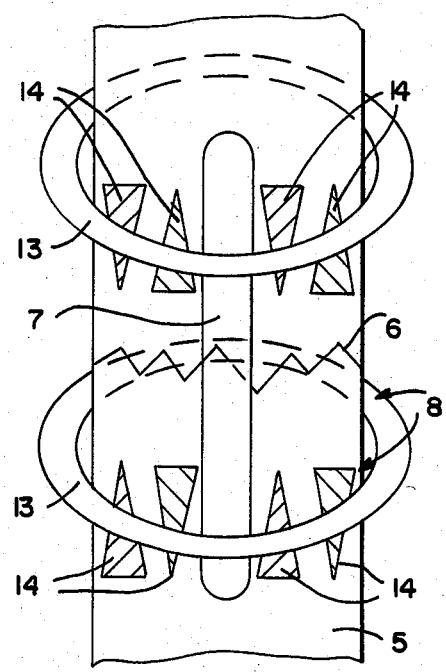

In FIG. 2g is given such an embodiment of the surgical device, where the at least partially resorbable osteosynthesis plate 7 has been fixed and tightened to its place by means of fixing elements 8" which consist of ring-shaped organs 13 and strain wedges 14 or corresponding which are located between bone 5 and organs 13. The ring-shaped organ 13 can be placed into the position shown in FIG. 2g through the fracture 6. (So this embodiment can be applied when the ends of bone 6 are apart of each other at the fracture). After the organs 13 are located around the bone they are tightened by means of wedges 14. Ring-shaped organ 13 can be manufactured also of biostable material and the wedges or corresponding organs can be manufactured favourably of resorbable material. Then the surgical device loses during healing its stiffness when the resorption of osteosynthesis plate 7 and wedges proceeds and stress is progressively transferred to bone, which for its part promotes healing.

According to a favourable embodiment of FIG. 2f the osteosynthesis plate 7 is placed totally inside of the bone, which will be immobilized, into the channel 11 which has been drilled through the fracture plane. The osteosynthesis plate gives in this case for the construction the necessary transverse stiffness. The fixation of fracture and longitudinal stiffness is confirmed by means of fixing elements 8 which are threaded through holes 10 which are drilled on both sides of the fracture plane. The fixing elements are tightened and knot to ring-shaped structures. If to the fracture are directed strong torsional stresses one can use e.g. two plates, which are located into the channels which are drilled through the fracture plane.

Figure 2H:
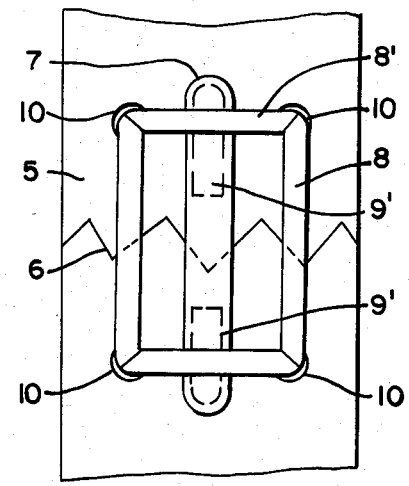
Figure 2I:
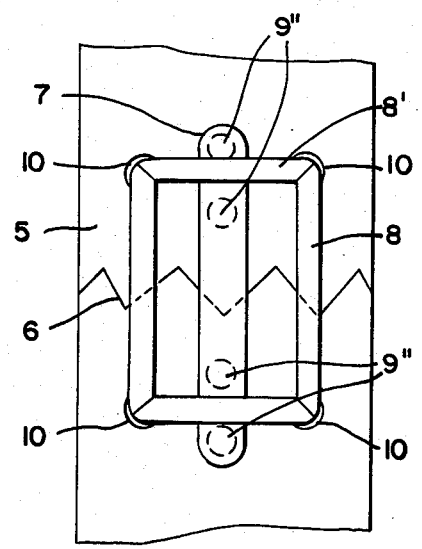
Figure 3A:
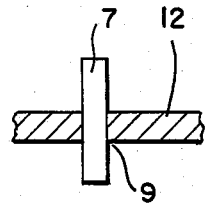
FIGS. 3a–3h show some forms of the cross-section of the osteosynthesis plate and FIGS. 4a–4b show an application of the device in the EXAMPLE 1.
Figure 3B:
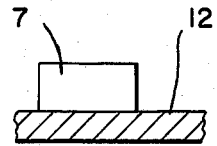
Figure 3C:
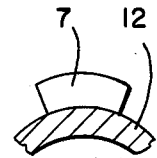
Figure 3D:
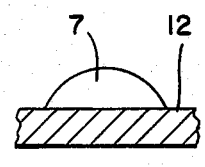
Figure 3E:
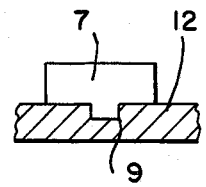
Figure 3F:
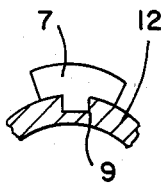
Figure 3G:
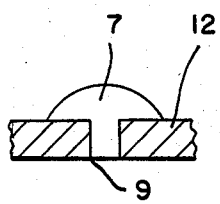
Figure 3H:
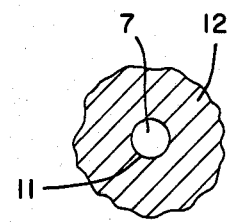

FIGS. 2h and 2i show alternative embodiments of the groove. FIG. 2h shows two-piece groove 9' at different sides of the fracture 6. Thus the groove 9' does not go beyond the fracture line. The corresponding support beam of the plate 7 is also two-piece, the length and other dimensions corresponding the same of the groove. FIG. 2i shows a groove 9" formed out of several holes and the plate 7 comprise the same amount of tap-formed support beams, which fit into the holes. The holes are not in the area of fracture 6. In both of these cases (2h and 2i) the operation does not concern the fracture itself and thus healing process is not disturbed by the formation of the groove. On the other hand the supporting effect of the plate 7 is not largely diminished.

When needed it is possible also in other cases of FIG. 2 to use two or more osteosynthesis plates.

The fixing elements can prevent tensile deformation of fracture directly as e.g. in FIGS. 2a and 2f or indirectly through osteosynthesis plate as e.g. in FIGS. 2b and 2c or both directly and indirectly as e.g. in FIGS. 2d and 2e.

Osteosynthesis plate 7 can be manufactured of resorbable material. It can contain additionally resorbable reinforcing fibers. It can contain also biostable fibers, such as carbon fibers, in the case of partially resorbable osteosynthesis plate. Additionally osteosynthesis plate can contain fillers and other additives etc. which are necessary for manufacturing process or for the use of plates.

FIG. 3 shows some typical forms of cross-section of osteosynthesis plate 7. Its cross-section can be e.g. rectangle 3a, 3b, 3e, curved 3c, 3f, rounded 3h or semicircle 3d, 3g or it can have some other form which is favourable from the point of view of bending strength. The rectangular plate can be located at least partially into a groove 9 or partially into grooves 9' 9" at different sides of the fracture 6. The grooves are done into the bone and the plate may have similar organs e.g. a longitudinal supporting beam (e.g. FIGS. 3e-3g), which is located into the groove 9. The lined region 12 of FIG. 3 represents part of the cross-section of the immobilized bone.

The fixing element 8, 8', 8" can be resorbable and/or biostable bundle of fibers, cord, braid, thread, yarn or band or some other corresponding structure or fiber construction. This structure can be also impregnated with monomer or polymer which also can polymerize or stiffen during the installation operation or after it.

The invention and its function is further illustrated by the following example.

EXAMPLE 1

Figure 4A:
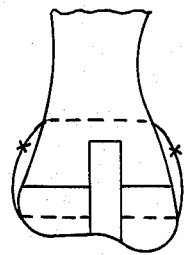
Figure 4B:
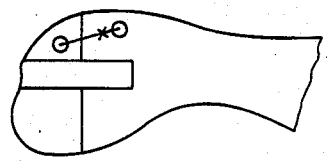

Compression moulding (T=230° C., compression pressure 1-2 ton/cm$^2$, compression time 7 min) was applied to manufacture about high molecular weight polyglycolide (a resorbable polymer) cylindrical resorbable osteosynthesis plates with length of 10 mm and cross-sectional radius of 1 mm. For the series of 20 rabbits osteotomy was performed to the distal part of femur in such a way that part of back cortex of bone remained as a hinge. On both sides of the plane of osteotomy holes (yarn channels) were drilled perpendicular to the long axis of bone. From the knee joint a 10 mm long hole (drill channel) with the diameter of 2 mm was drilled into the direction of long axis of bone. The osteotomy was immobilized with the polyglycolide plate, which was pressed into the drill channel, and with the fixing element consisting of resorbable Dexon ® sutures which were threaded into the yarn channels, tightened and knotted (FIGS. 4a and 4b).

In the series 20 rabbits were operated. These were divided into four different groups each containing 5 rabbits. After 3, 6, 12 and 24 weeks the groups were sacrificed one after the other. The operated limbs were compared with the healthy ones by means of x-ray techniques. The things which were examined in x-ray figures were: the endurance of fixation, the ossifying, the incorrect positions of axis-direction of bone and arthrotic changes of the whole knee joint.

The fixation holded in 19 cases (95%). In one case there was a joint of connective tissue. In one case arthrotic changes were observed. In this case there was an infection after fixation operation: the fixation holded and the osteotomy ossified, but into the knee-joint were formed arthrotic changes. An erroneous position of the axis direction of bone was found in no case.

Accordingly 95% of fixations of osteotomy succeeded in the test series.

The resorption of the surgical device was also followed and it was found that the fixing element (Dexon ® sutures) was resorbed nearly completely and the yarn channels were filled with new bone nearly completely after 24 weeks. It was found that the resorption of polyglycolide plates was started distinctly after 12 weeks and after 24 weeks about 50% of their mass was resorbed and the resorption was still continuing.

We claim:

1. A surgical device for immobilization of a bone fracture, which surgical device has at least one organ which goes beyond or perforates the fracture and is in connection with the parts of bone on opposite sides of the fracture, said surgical device comprising:

at least one, at least directly after a surgical installation operation, essentially stiff and at least partially resorbable osteosynthesis plate or beam which is constructed at least partially of resorbable organic polymeric material(s) and is positioned to go beyond or perforate the fracture; and, at least one fixing element which is flexible at least during a stage of installation, is constructed at least partially of fibrous material and is fastened to bone and/or tightened to its place to go beyond or to perforate the fracture and/or to go beyond or to perforate the osteosynthesis plate or beam in such a way that the osteosynthesis plate or beam, the fixing element and a region of immobilized bone where the fracture exists form an assembly whose stiffness is high enough to confirm the healing of the fracture, the resorption characteristics of said at least partially resorbable osteosynthesis plate or beam being such that during the healing of the fracture the stiffness and mechanical strength of the surgical device decreases as the stiffness and mechanical strength of the healing fracture increases and after the healing of the fracture there is no need to remove the surgical device or a part of it at a separate subsequent operation.

2. Surgical device of claim 1 characterized in that into the bone has been formed at least one groove and/or hole or the like and into which the osteosynthesis plate or beam is located at least partially, the osteosynthesis plate or beam being shaped in such a way that it fits at least partially into the groove and/or into the hole or the like and comprising means the shape of which corresponds to the form of the groove or the shape of its cross-section comprising essentially the form of the groove and/or the hole.

3. Surgical device as claimed in any one of claims 1 and 2, characterized in that the fixing element is tightened around the bone.

4. Surgical device as claimed in any one of claims 1 and 2, characterized in that into the bone has been formed at least one hole or notch and the fixing element is tightened between the hole or notch and the outer surface of bone and/or between a plurality of holes or notches.

5. Surgical device as claimed in claim 3, characterized in that the fixing element comprises an assembly which is composed of at least one ring-shaped organ which is manufactured of fibers or fiber reinforced polymer and of strain wedges which are located between the bone and the ring-shaped organ.

6. Surgical device as claimed in claim 1, characterized in that the fixing element is thread-like and is formed to ring-shape by tightening it and by forming into it at least one knot or the like.

7. Surgical device as claimed in any one of claims 1 and 2 characterized in that the fixing element is formed by combining fibers mechanically and/or chemically to each other to provide a thread-like or the like structure.

8. Surgical device as claimed in claim 7, characterized in that the fixing element is impregnated by a monomer or polymer and the fixing element is flexible at least during the installation operation.

9. Surgical device as claimed in claims 1 or 2, characterized in that the fixing element is manufactured at least partially of resorbable material.

10. The surgical device of claim 1 or 2 in which said plate or beam and said fixing element are made of totally resorbable material(s).

11. The surgical device of claim 1 in which said polymeric material(s) include polyglycolides, polylactides or their copolymers.

12. The surgical device of claim 1 in which the fibrous material of said flexible fixing element is coated or impregnated with a polymer, reactive oligomer or monomer.

13. The surgical device of claim 12 in which said polymer, reactive oligomer or monomer is at least partially resorbable.

14. The surgical device of claim 1 in which the fibrous material of said flexible fixing element is at least partially resorbable.

15. A method of immobilizing and closing a fracture in living bone with a surgical device having at least one organ which goes beyond or perforates the fracture and is in connection with the parts of bone on opposite sides of the fracture, said method comprising:

positioning at least one at least partially resorbable osteosynthesis plate or beam so that it goes beyond or perforates the fracture, said plate or beam being constructed at least partially of resorbable organic polymeric material(s) and being essentially stiff at least directly after a surgical installation operation; and, fastening to bone and/or tightening to its place to go beyond or to perforate the fracture and/or to go beyond or to perforate said plate or beam at least one fixing element which is flexible at least during a stage of installation and is constructed at least partially of fibrous material, said osteosynthesis plate or beam, a region of immobilized bone where the fracture exists and said at least one fixing element when fastened to bone and/or tightened to its place forming an assembly whose stiffness is high enough to confirm the healing of the fracture, and the resorption characteristics of said at least partially resorbable osteosynthesis plate or beam being such that during the healing of the fracture the stiffness and mechanical strength of the surgical device decreases as the stiffness and mechanical strength of the healing fracture increases and after the healing of the fracture there is no need to remove the surgical device or a part of it at a separate subsequent operation.

* * * * *